US008897522B2

(12) United States Patent
Mestha et al.

(10) Patent No.: US 8,897,522 B2
(45) Date of Patent: Nov. 25, 2014

(54) PROCESSING A VIDEO FOR VASCULAR PATTERN DETECTION AND CARDIAC FUNCTION ANALYSIS

(75) Inventors: Lalit Keshav Mestha, Fairport, NY (US); Beilei Xu, Penfield, NY (US); Edgar A. Bernal, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 357 days.

(21) Appl. No.: 13/483,992

(22) Filed: May 30, 2012

(65) Prior Publication Data
US 2013/0322729 A1 Dec. 5, 2013

(51) Int. Cl.
*G06K 9/00* (2006.01)
*A61B 5/02* (2006.01)

(52) U.S. Cl.
USPC .......................................... 382/128; 600/479

(58) Field of Classification Search
None
See application file for complete search history.

(56) References Cited

U.S. PATENT DOCUMENTS

| | | | | |
|---|---|---|---|---|
| 4,238,760 | A * | 12/1980 | Carr | 257/443 |
| 5,699,797 | A * | 12/1997 | Godik | 600/475 |
| 6,996,288 | B2 * | 2/2006 | Sun | 382/274 |
| 8,630,465 | B2 * | 1/2014 | Wieringa et al. | 382/128 |
| 2001/0027273 | A1 * | 10/2001 | Flock et al. | 600/473 |
| 2003/0018271 | A1 * | 1/2003 | Kimble | 600/473 |
| 2005/0148876 | A1 * | 7/2005 | Endoh et al. | 600/454 |
| 2006/0257031 | A1 * | 11/2006 | Abramoff et al. | 382/224 |
| 2006/0269111 | A1 * | 11/2006 | Stoecker et al. | 382/128 |
| 2009/0028461 | A1 * | 1/2009 | Wieringa et al. | 382/284 |
| 2009/0052738 | A1 * | 2/2009 | Qureshi et al. | 382/103 |
| 2009/0067695 | A1 * | 3/2009 | Komiya et al. | 382/128 |
| 2010/0177184 | A1 * | 7/2010 | Berryhill et al. | 348/77 |
| 2011/0251493 | A1 | 10/2011 | Poh et al. | |
| 2011/0295062 | A1 * | 12/2011 | Gratacos Solsona et al. | 600/109 |
| 2012/0071765 | A1 * | 3/2012 | Chinnock | 600/476 |
| 2013/0171599 | A1 * | 7/2013 | Bleich et al. | 434/247 |
| 2014/0112559 | A1 * | 4/2014 | Freeman et al. | 382/128 |

FOREIGN PATENT DOCUMENTS

WO WO 0115597 A1 * 3/2001

OTHER PUBLICATIONS

"Contact-Free Measurement of Cardiac Pulse Based on the Analysis of Thermal Imagery," Marc Garbey et al, IEEE Transactions on Biomedical Engineering, vol. 54, No. 8, Aug. 2007, pp. 1418-1426.*

(Continued)

*Primary Examiner* — Wenpeng Chen
(74) *Attorney, Agent, or Firm* — Philip E. Blair; Fleit Gibbons Gutman Bongini & Bianco P.L.

(57) ABSTRACT

What is disclosed is a non-contact system and method for determining cardiac function parameters from a vascular pattern identified from RGB and IR video signals captured simultaneously of a region of exposed skin of a subject of interest. In one embodiment, a video of a region of exposed skin is captured using a video camera that captures color values for pixels over visible channels and an IR camera that measures pixel intensity values in wavelength ranges of interest. Pixel intensity values are processed to generate a vascular binary mask that indicates pixel locations corresponding to the vascular pathways. The IR images are registered with corresponding data from the camera's visible channels such that pixels that correspond to the vascular pattern can be isolated in each frame of the video of visible color data. Once processed, pixels associated with the isolated vascular patterns are analyzed to determine desired cardiac function parameters.

22 Claims, 9 Drawing Sheets

(56) References Cited

OTHER PUBLICATIONS

"Remote Non-invasive Stereoscopic Imaging of Blood Vessels: First In-vivo Results of a New Multispectral Contrast Enhancement Technology," F. P. Wieringa et al., Annals of Biomedical Engineering, vol. 34, No. 12, Dec. 2006 pp. 1870-1878.*

Wei Lu et al., "Approach and Applications of Constrained ICA", IEEE Transactions on Neural Networks, vol. 16, No. 1, Jan. 2005.

Wei Lu et al., "Constrained Independent Component Analysis", School of Computer Engineering, Nanyang Technological University, Singapore 639798.

Takano et al., "Heart rate measurement based on a time-lapse image", Medical Engineering & Physics 29 (2007), pp. 853-857, www.sciencedirect.com.

Poh, et al., "Non-contact, automated cardiac pulse measurements using video imaging and blind source separation.", May 10, 2010, vol. 18, No. 10 / Optics Express 10762.

J. Lee, et al., "Temporally constrained ICA-based foetal ECG separation", Electronics Letters, Oct. 13, 2005, vol. 41, No. 21.

Mestha et al., "Estimating Cardiac Pulse Recovery From Multi-Channel Source Data Via Constrained Source Separation", U.S. Appl. No. 13/247,683, filed Sep. 28, 2011.

Jean-Francois Cardoso, "Blind signal separation: statistical principles", pp. 1-16, (Official Version published as: Proceedings of the IEEE, vol. 9, No. 10, pp. 2009-2025, Oct. 1998).

Hyvarinen et al., "Independent Component Analysis: Algorithms and Applications", Neural Networks Research Centre, Helsinki University of Technology, Finland, Neutral Networks, pp. 1-31, 13(4-5); 411-430, 2000.

Mestha et al., "Filtering Source Video Data Via Independent Component Selection", U.S. Appl. No. 13/281,975, filed Oct. 26, 2011.

Dalal et al., "Histograms of Oriented Gradients for Human Detection", Proceedings of the Conference on Computer Vision and Pattern Recognition, San Diego, California, USA, pp. 886-893, (2005).

Mestha et al., "A Multi-Filter Array for a Multi-Resolution Multi-Spectral Camera", U.S. Appl. No. 13/239,642, filed Sep. 22, 2011.

Skaff et al., "Estimating a Visible Vector Representation for Pixels in an Infrared Image", U.S. Appl. No. 13/364,835, filed Feb. 2, 2012.

Xu et al., "Subcutaneous Vein Pattern Detection Via Multi-Spectral IR Imaging in an Identity Verification System", U.S. Appl. No. 13/087,850, filed Apr. 15, 2011.

Mestha et al., "Deriving Arterial Pulse Transit Time From a Source Video Image", U.S. Appl. No. 13/401,286, filed Feb. 21, 2012.

Mestha et al., "Removing Environment Factors From Signals Generated From Video Images Captured for Biomedical Measurements", U.S. Appl. No. 13/401,207, filed Feb. 21, 2012.

Piratla et al., "Web-Based System and Method for Video Analysis", U.S. Appl. No. 13/417,979, filed Mar. 12, 2012.

Xu et al., "Monitoring Respiration With a Thermal Imaging System", U.S. Appl. No. 13/103,406, filed May 9, 2011.

Wang et al., "Multi-Band Infrared Camera System Optimized for Skin Detection", U.S. Appl. No. 13/416,436, filed Mar. 9, 2012.

Mestha et al., "Systems and Methods for Non-Contact Heart Rate Sensing", U.S. Appl. No. 13/247,575, filed Sep. 28, 2011.

* cited by examiner

PROCESSING A VIDEO FOR VASCULAR PATTERN DETECTION AND CARDIAC FUNCTION ANALYSIS

TECHNICAL FIELD

The present invention is directed to systems and methods which capture video images of a region of exposed skin such as an arm, chest, neck, etc., of a subject of interest; analyze that video to identify a vascular pattern in that region; and then process the pixels associated with the identified vascular pattern to determine various cardiac functions for the subject.

BACKGROUND

Monitoring cardiac events is of clinical importance in the early detection of potentially fatal conditions. Current technologies involve contact sensors the individual must wear constantly. Such a requirement can lead to patient discomfort, dependency, loss of dignity, and further may fail due to a variety of reasons including refusal to wear the monitoring device. Elderly patients and those suffering from cardiac conditions are even more likely to suffer from the adverse effects of continued monitoring. Unobtrusive, non-contact, imaging based methods are increasingly needed for monitoring cardiac function.

Accordingly, what is needed in this art is a system and method for determining cardiac function from video images captured of a region of exposed skin of a subject of interest.

INCORPORATED REFERENCES

The following U.S. Patents, U.S. Patent Applications, and Publications are incorporated herein in their entirety by reference.

"Multi-Band Infrared Camera System Optimized For Skin Detection", U.S. patent application Ser. No. 13/416,436, by Wang et al.

"A Multi-Filter Array For A Multi-Resolution Multi-Spectral Camera", U.S. patent application Ser. No. 13/239,642, by Xu et al, (now issued on Dec. 3, 2013 as U.S. Pat. No. 8,600,227).

Subcutaneous Vein Pattern Detection Via Multi-Spectral IR Imaging In An Identity Verification System", U.S. patent application Ser. No. 13/087,850, by Xu et al.

"Deriving Arterial Pulse Transit Time From A Source Video Image", U.S. patent application Ser. No. 13/401,286, by Mestha (now published on Aug. 22, 2013 as US patent application publication 2013/0218028).

"Estimating Cardiac Pulse Recovery From Multi-Channel Source Data Via Constrained Source Separation", U.S. patent application Ser. No. 13/247,683, by Mestha et al.

"Systems And Methods For Non-Contact Heart Rate Sensing", U.S. patent application Ser. No. 13/247,575, by Mestha et al.

"Filtering Source Video Data Via Independent Component Selection", U.S. patent application Ser. No. 13/281,975, by Mestha et al.

"Removing Environment Factors From Signals Generated From Video Images Captured For Biomedical Measurements", U.S. patent application Ser. No. 13/401,207, by Mestha et al.

BRIEF SUMMARY

What is disclosed is a non-contact system and method for determining cardiac function parameters from a vascular pattern identified from RGB and/or IR video signals captured simultaneously of a region of exposed skin of a subject of interest. In one embodiment, a video of a region of exposed skin is captured using a video camera that captures color values for pixels over visible channels corresponding generally to the primary visible colors (typically RGB) and an infrared (IR) camera that measures pixel intensity values in one or more wavelength ranges of interest. Pixel intensity values acquired by the IR channel are processed to generate a vascular binary mask that indicates the location of pixels corresponding with the vascular pathway of the subject. The IR image frames are then registered with the corresponding data obtained by the camera's visible channels such that pixels that correspond to the subject's vascular pattern can be isolated in each frame of the video sequence of visible color data. The process can be carried out frame-by-frame for all frames from the IR channel or selected frames at a predefined time interval or triggered by an event such as detected motion from object-of-interest either in the visible channel or IR channel. For non-consecutive vascular pathway detection, the detected vascular pattern can be propagated through the frame until a new update is received. Once processed, pixels associated with the isolated vascular patterns are analyzed on a frame-by-frame basis or with selected frames such that cardiac function information being carried by those pixels can be processed to determine desired cardiac function parameters. With an implementation of the teachings hereof, vascular patterns can be quickly discovered in a region of exposed skin and isolated, and cardiac function parameters determined in real-time (or processed offline) without disturbing the resting cardiac patient. The system and methods disclosed herein provide an effective tool for arterial and vein pattern study and cardiac function analysis.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which:

FIG. 6 compares power content in signals with respect to heart beat frequency from pixels obtained without vascular pattern isolation (FIG. 6A) and then using only pixels which were identified as being associated with blood vessels of the identified vascular pattern (FIG. 6B);

DETAILED DESCRIPTION

What is disclosed is an unobtrusive, non-contact system and method for determining cardiac function parameters from pixels associated with a vascular pattern identified in RGB and IR video signals captured simultaneously of a region of exposed skin of a subject of interest.

NON-LIMITING DEFINITIONS

A "video", as used herein, refers to a time varying video signal, as is known in the arts, comprising a temporal sequence of image frames of a subject of interest. Such a video may also contain additional components such as, for example, an audio signal and a time reference signal. The size of the video data may get large for longer video sequences. For those systems which are resource limited, captured video comprising a 2-dimensional array of image frames can be projected onto a lower dimensional subspace to reduce the dimensionality of the data and performing Independent component analysis (ICA) on the projected data wherein independent components in the signals are identified. It should be appreciated that this is not an invertible operation. Such a method is disclosed in the above-incorporated U.S. Patent Application entitled: "Filtering Source Video Data Via Independent Component Selection" by Mestha et al.

A "subject of interest" refers to any subject having a network of subcutaneous blood vessels beneath skin tissue. Terms used herein such as 'person' or 'patient' are not to be viewed as limiting the scope of the appended claims solely to human subjects. Subjects include mammals, birds, reptiles, fish, and even certain insects.

A "region of exposed skin" is an unobstructed area of the subject's skin. Such regions can be identified in image frames of a video using, for example, object identification, pixel classification, material analysis, texture identification, and pattern recognition methods.

Figure 1:
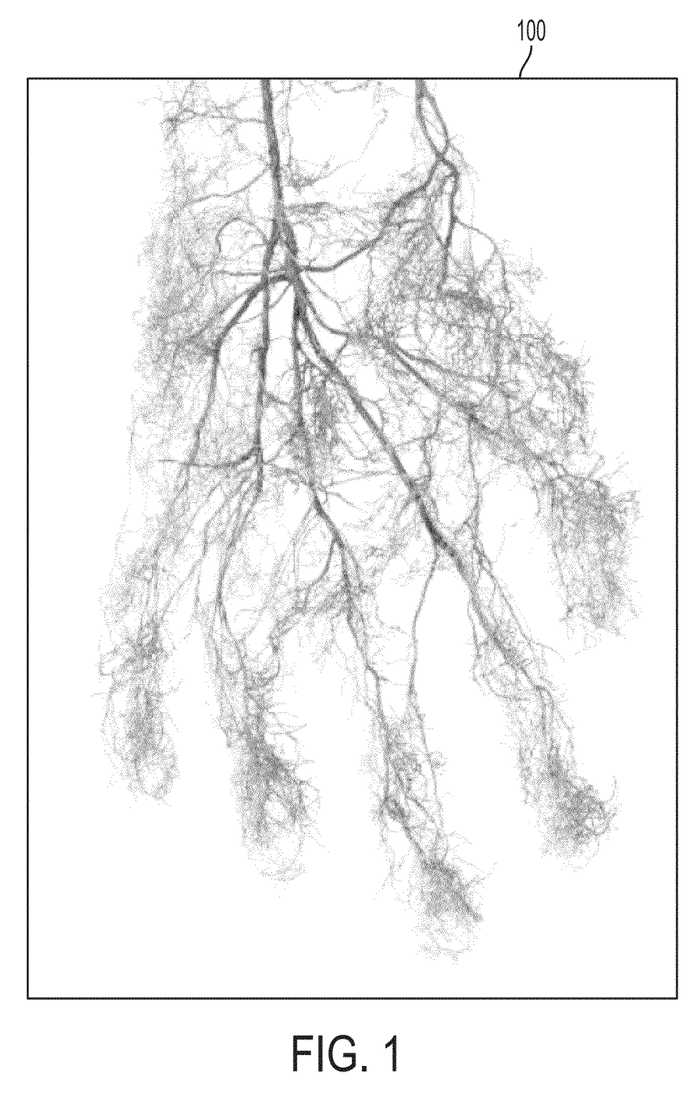
FIG. 1 shows an image of a vascular pattern beneath a region of exposed skin of a human hand.

A "vascular pattern" refers to a subcutaneous network of vessels (veins, arteries, capillaries, arterioles, etc.) which transport blood throughout the subject's body. FIG. 1 shows an image 100 of a vascular pattern beneath a region of exposed skin of a human hand.

Figure 2:
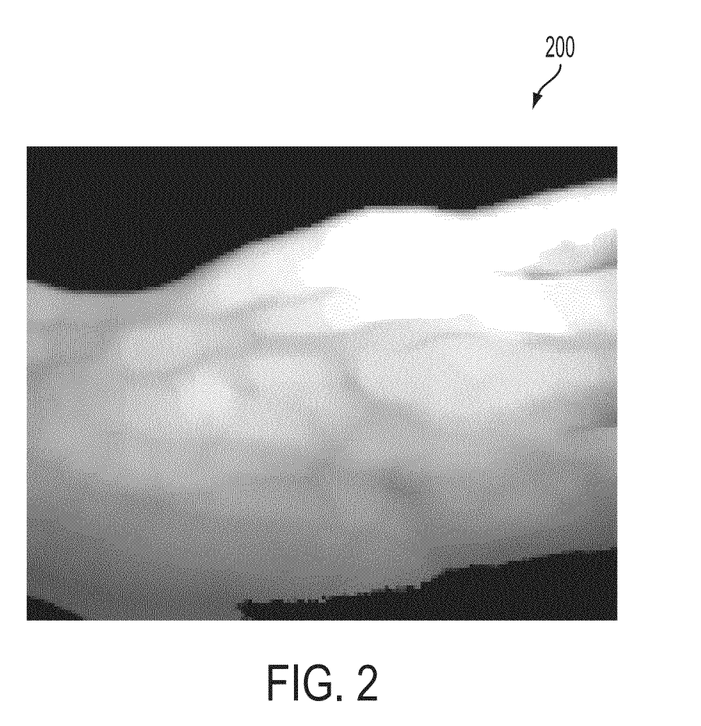
FIG. 2 shows an IR image wherein a vascular pattern of the back of a human hand is seen under NIR illumination.
Figure 3A:
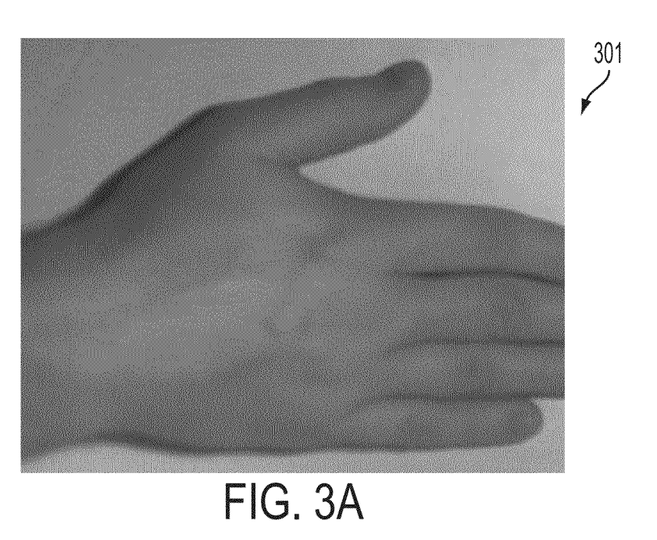
FIGS. 3A-B shows an image of a human hand (3A) and an image containing on-pixels associated with the subject's vascular pattern (3B)
Figure 3B:
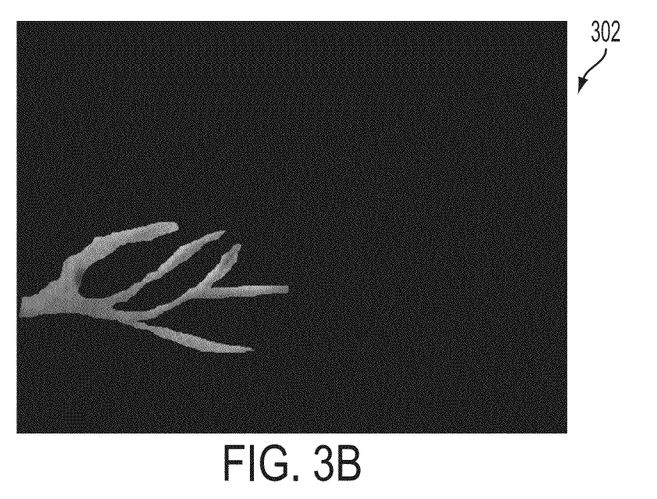

A "vascular binary mask" is a binary image that indicates the location of pixels corresponding with the subject's vascular pattern with pixel values equal to 1 and 0. In one embodiment, if pixel locations correspond to the vascular pattern then they are assigned a value of 1, and assigned a value of 0 if they do not correspond. Other embodiments may use different values for the binary mask. A subject's vascular pattern contains blood vessels which transport hemoglobin. Hemoglobin has a high absorption rate in the near infrared (NIR) when compared to other tissues. Under IR illumination, the subject's vascular pattern can be detected in a set of IR images due to differences in absorption rates, and mapped. FIG. 2 shows an IR image 200 wherein a vascular pattern of the back of a human hand is seen under NIR illumination. FIGS. 3A-B show an image 301 of a human hand and a corresponding image 302 of the hand in image 301 containing on-pixels associated with the subject's vascular pattern.

A "cardiac function parameter" refers to a parameter relating to the subject's cardiac function. Parameters include arterial pulse, cardiac pulse frequency, pulse transit time, cardiac output, blood pressure, vessel diameter, blood density, vessel blockage, and peripheral neuropathy. A cardiac function parameter, when provided as output, may take a variety of forms including, for example, a curve, plot, chart, graph, text, a numeric or binary value, an audible sound, and the like, and may further comprise modifications having been made to the source video signal as a result of processing. Cardiac function parameters may be communicated in a variety of ways including, for example, email, voicemail, text messaging, hardcopy print, graphical display, a web page, a webpage where the user can download the results, or a document where the user can view, edit, modify, and annotate the results. Communicating the result to the user is intended to include communicating the results to a third party and storing the results to a storage device or to a remote device over a local or wide area network. A fee may be associated with obtaining a subject's cardiac function parameters and/or for providing such results to a user or to a third party.

"Arterial pulse" is a pressure wave created by the subject's heart contracting and pushing blood through the vascular network. An arterial pulse generally comprises a forward wave generated when the contraction and a reflected wave returning from the periphery. This wave pressing on the walls of the subject's blood vessels as the heart beats correlates to the subject's blood pressure.

"Pulse frequency" is the frequency of the pulse pressure wave generally given in beats per minute (bpm). An adult human's cardiac pulse frequency is around 72 bpm. Each species has their own normal pulse frequency range.

"Cardiac output" refers to the volume of blood the heart muscle can pump and is generally expressed in L/min. In an adult human, the cardiac output is approximately 5 L/min. Cardio output is given by: $CO=SV \cdot HR$, where SV is stroke volume, and HR is heart rate in bpm. Stroke volume can be affected by valvular dysfunction and ventricular geometric form.

"Pulse transit time" refers to the time it takes the pulse pressure wave to travel from a proximal location (upstream) to a distal location (downstream) in the subject's vascular network. Pulse transit time (PTT) is a function of wave velocity which, in turn, is a function of blood pressure, vessel diameter, and blood density. Localized PTT is used as an indirect marker of various pathologic conditions such as, for example, vessel blockage between two points and peripheral neuropathy.

Figure 4:
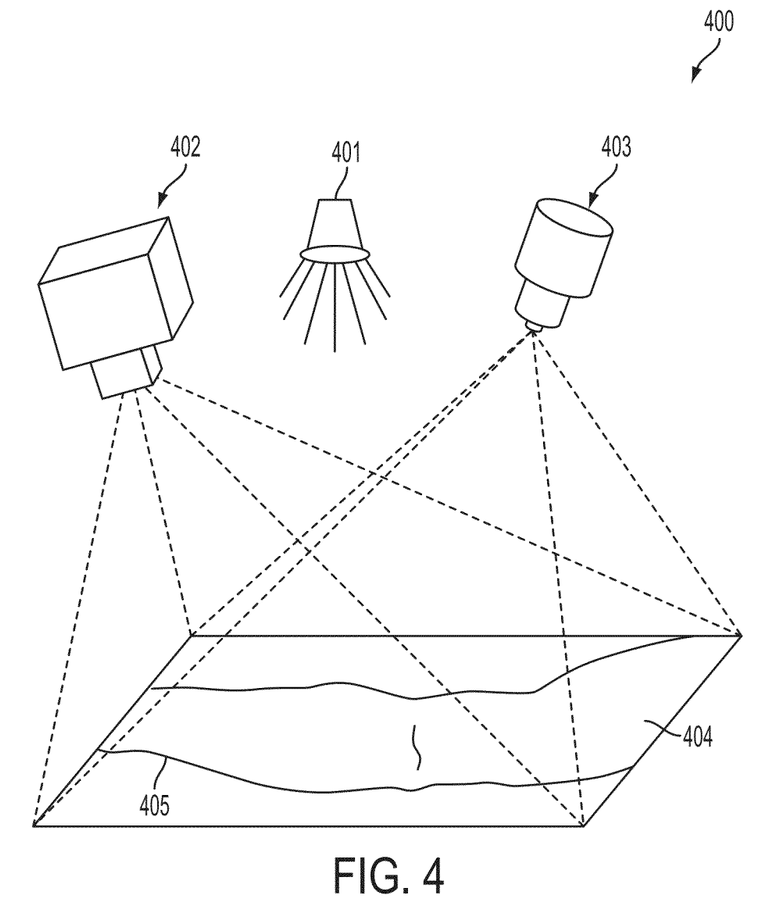
FIG. 4 shows an example video system comprising an illumination source, a 3-channel RGB camera, and a single NIR camera for capturing RGB and IR video 404 of a subject's arm.

A "video system" is a device for capturing a video of a subject of interest. As used herein, a video system comprises at least one video device for capturing images in the visible spectrum corresponding generally to the primary visible colors (typically RGB), and at least one IR video camera for capturing IR images in any of: the near infrared (NIR), short wave infrared (SWIR), mid-wave infrared (MWIR), and long wave infrared (LWIR) wavelength ranges. The IR video camera may further comprise a multi-spectral or hyper-spectral video camera. Such cameras may comprise a processor for executing machine readable program instructions and a storage device such as a memory, and may further include a plurality of outputs for outputting data on a per-channel basis. The video system may be a hybrid camera capable of operating in a conventional video mode with high frame rates and high spatial resolution and in a spectral mode with low frame rates and high spectral resolution. Video systems comprising color cameras and spectral sensors are available from a variety of vendors in various streams of commerce. FIG. 4 shows an example video system 400 comprising an illumination source 401, a 3-channel RGB camera 402, and a single NIR camera 403 for capturing RGB and IR video 404 of a subject's arm 405. Illumination source 401 may be configured to project light onto the subject's arm; alternatively, illumination source 401 may represent ambient light. The video system of FIG. 4 may comprise a camera system where the RGB camera and the IR camera have been integrated into a single composite video capture device. Conversely, individual video cameras are used for each of the desired visible channels, i.e., R, G, and B, and for each of the desired IR wavelength ranges of interest. Such a video system may further comprise a video analysis module as described herein with respect to FIG. 8.

A "video analysis module", in one embodiment, is a hardware device with at least one processor executing machine readable program instructions for analyzing video images to isolate a vascular pattern from the image frames on a frame-by-frame basis, and determine cardiac function parameters from pixels corresponding to blood vessels in that pattern. Such a module may comprise, in whole or in part, a software application working alone or in conjunction with one or more hardware resources. Such software applications may be executed by processors on different hardware platforms or emulated in a virtual environment. Aspects of the video analysis module may leverage off-the-shelf software. In various embodiments, analyzing the vascular patterns to determine cardiac function parameters involves independent component analysis.

"Independent Component Analysis" (ICA) is a decomposition method for uncovering independent source signal components from a set of observations that are composed of linear mixtures of the underlying sources, called "independent components" of the observed data. ICA uncovers these independent components (ICs) in the source signal by looking for statistically independent factors in the data (as opposed to uncorrelated factors). The order of the resulting uncovered independent components is arbitrary. In general, ICA has an inherent indeterminacy that cannot be reduced further without additional constraints. In accordance with various embodiments hereof, the independent components obtained via ICA are used, in turn, to determine cardiac function parameters.

A "remote sensing environment" refers to a non-contact, unobtrusive non-invasive means of acquiring data from a subject, i.e., the sensing device does not physically contact the subject being sensed. The sensing device can be any distance away from the subject, for example, as close as less than an inch to as far as miles in the case of telemedicine. The teachings hereof find their intended uses in such a remote sensing environment such that the resting cardiac patient remains undisturbed.

Flow Diagram of Example Embodiment

Figure 5:
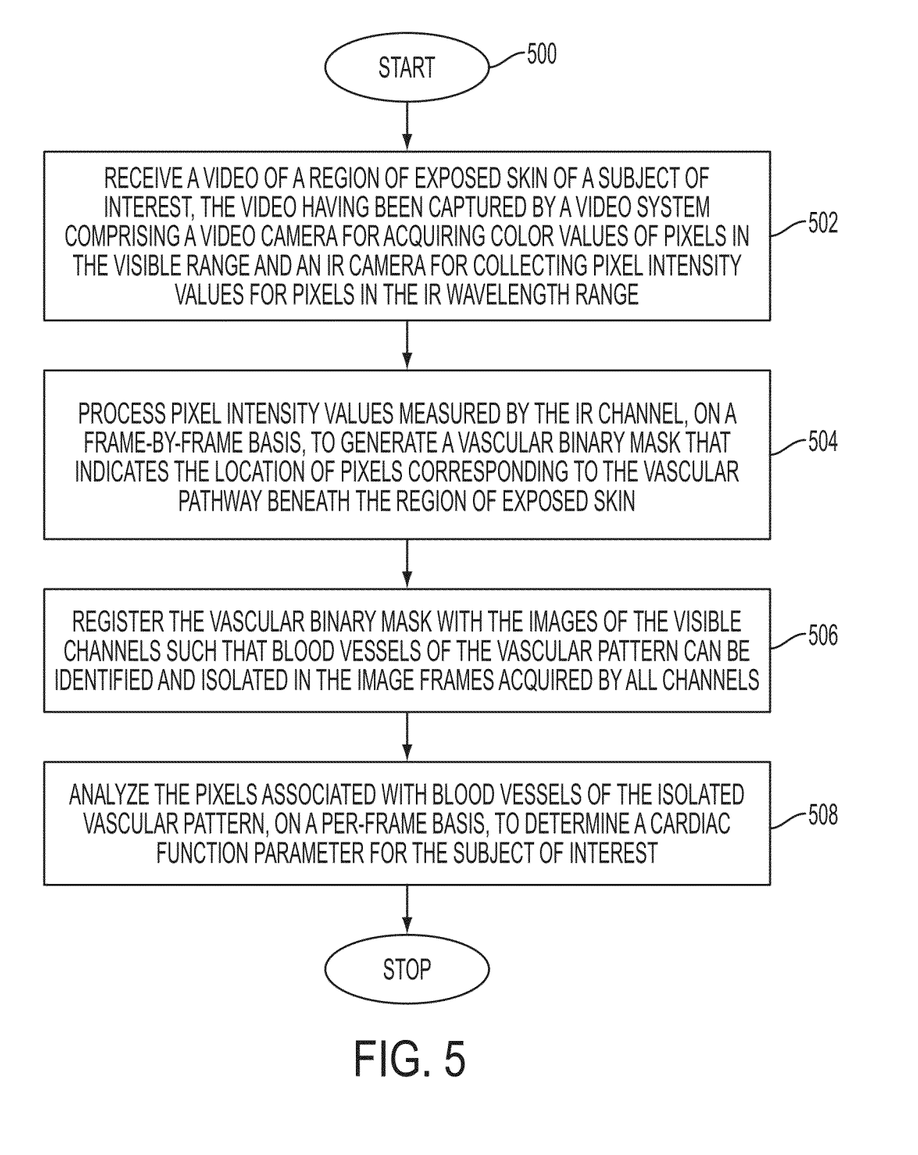
FIG. 5 is a flow diagram illustrating one embodiment of the present method for analyzing a video of a subject of interest to determine a cardiac function parameter in a non-contact remote sensing environment.

Reference is now being made to the flow diagram of FIG. 5 which illustrates one example embodiment of the present method for analyzing a video of a subject of interest to determine cardiac function parameters in a remote sensing environment. Flow processing begins at step 500 and immediately proceeds to step 502.

At step 502, a video is received of a region of exposed skin of a subject of interest being monitored for cardiac function. The video has been captured using a video system comprising at least one video camera that outputs data comprising color values collected for pixels by at least one visible channel and at least one infrared video camera that outputs data comprising intensity values collected for pixels over at least one infrared channel. One example video system which simultaneously captures video in both the visible and infrared wavelength ranges is shown in FIG. 4. For vascular pathway detection, the infrared video may be pre-processed to compensate for non-uniform illumination due to a curvature of a surface of the region of exposed skin. The video may be processed to compensate for motion induced blur, imaging blur, or slow illuminant variation. Smoothing may be performed to remove skin texture from a surface of the region of exposed skin. Smoothing can be effectuated using, for example, a Gaussian smoothing, as is well understood. The video may be processed to enhance contrast or brightness. Independent component selection can also be used to emphasize certain content in the video such as, for example, a region containing larger blood vessels. If camera-related noise or environmental factors are adversely affecting extraction of cardiac signals, compensation can be effectuated using the teachings described in the above-incorporated reference: "Removing Environment Factors From Signals Generated From Video Images Captured For Biomedical Measurements", by Mestha et al. Post-compensated video signals contain decorrelated and noise corrected channels on a per-frame basis.

At step 504, the pixel intensity values measured by the IR channel(s) are processed, on a frame-by-frame basis to generate a vascular binary mask that indicates the location of pixels corresponding to the vascular pathway of the subject within the region of exposed skin. Alternatively, such processing occurs on a designated frame basis or is triggered by an event such as detected subject motion. As discussed with respect to FIGS. 2 and 3, the subject's vascular pattern can be detected in a set of IR images due to differences in absorption rates of hemoglobin. The detected vascular pattern is mapped in each of the processed IR image frames.

At step 506, the IR frame is then registered with the pixel data of the visible channels such that blood vessels of the subject's vascular pattern can be isolated in each frame of the video for all data acquisition channels, (i.e., 3-channels of RGB data and 1-channel of IR data). Registering the IR frame with the visible channel data involves extracting features in the corresponding IR and visible frames, determining correspondence between the 2 sets of features, and modifying one frame (for example, by performing translation, rotation, or other geometric transformations such as affine and projective) so that the feature locations between the IR and visible frames match. Methods for extracting features and determining feature correspondence are well established. Once the pair of IR and visible image frames or a set of selected IR-visible frame pairs are registered, pixels in the visible channels corresponding to blood vessels of the vascular patterns can be isolated (and preferably extracted) for processing.

At step 508, the isolated pixels associated with blood vessels of the vascular pattern are then analyzed, on a per-frame or on a designated frame basis, to determine a desired cardiac function parameter for the subject in the video. Thereafter, in this particular embodiment, further processing stops. This can also be carried out at selected frames at a predefined time interval or triggered by an event such as object motion in the scene. The detected vascular pattern is propagated throughout the interval image frames.

Assume, for example, that the desired cardiac function parameter is pulse transit time. As such, proximal and distal regions of a blood vessel in the isolated vascular pattern need to be identified across image frames and processed to obtain a time-series signal for each channel. An average of all pixel values in each of the proximal and distal regions within each image frame is computed to obtain a channel average on a per-frame basis. A global channel average can then be computed, for each channel, by adding the channel averages across multiple image frames and dividing by the total number of frames. The channel average is then subtracted from the global channel average and the result divided by a global channel standard deviation to obtain a zero-mean unit variance time-series signal for each of the proximal and distal regions. The time-series signals contain frequency components. The time-series signals obtained for each of the proximal and distal regions are normalized preferably using values obtained from apriori knowledge of the subject's cardiac history. Once normalized, for each image frame, the time-series signals are subjected to a filtering to remove undesirable frequencies using, for example, a Fast Fourier Transform (FFT). The resulting processed and filtered time-series signals for each of the proximal and distal regions contain the sum total of volumetric pressure changes within each of those regions. Further processing can be done to extract, for instance, plethysmographic signals using independent component analysis. Arterial pulsations comprise a dominant component of these signals from which arterial pulse and pulse frequency, for instance, can be recovered.

The flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Performance Results

Figure 6A:
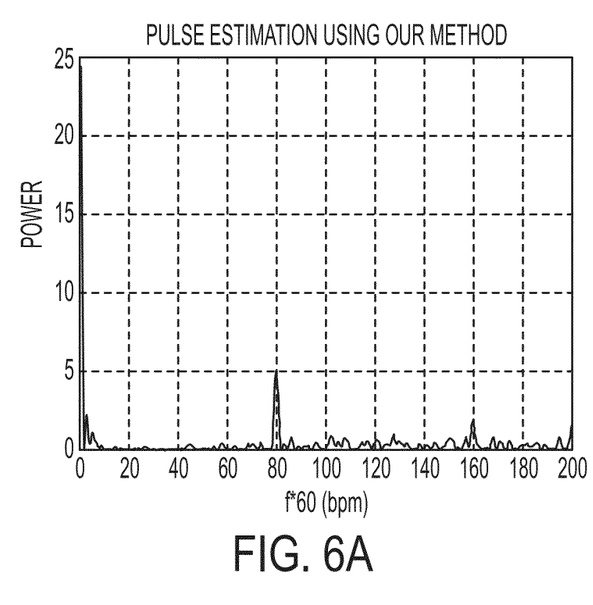
Figure 6B:
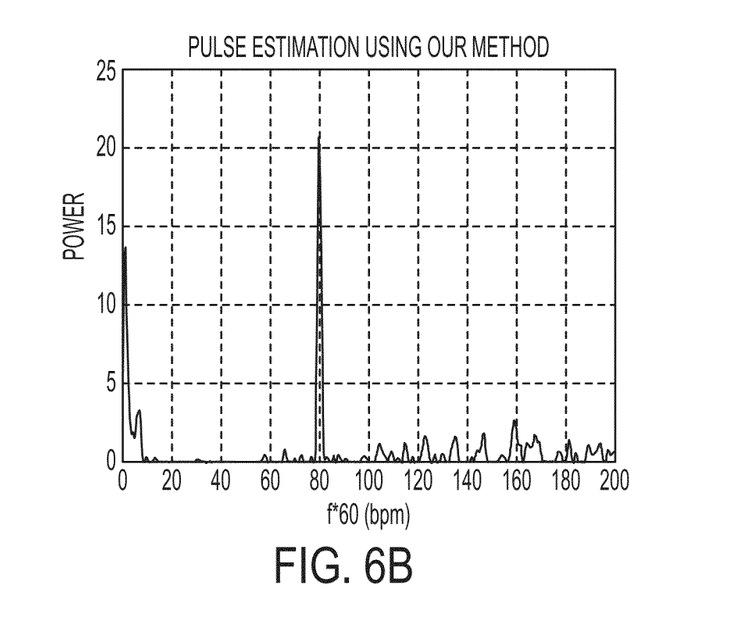

The present method consists of determining a location of pixels associated with blood vessels of a vascular pattern of a region of exposed skin area. Heart rate estimates are determined from pixel values obtained with and without vascular pattern identification. Actual heart rate was recorded at 77 to 81 bpm (mean value=79 bpm) using a finger oximeter. The plots of FIG. 6 compare heart rate estimates determined from pixels obtained without vascular pattern isolation (FIG. 6A) (i.e., from image 301 of FIG. 3) and then using only those pixels which have been identified as being associated with blood vessels of the vascular pattern (FIG. 6B) (i.e., from image 302 of FIG. 3). Clearly, signal strength is greatly improved and even further improvements are expected with increased development in devices which will provide full NIR data.

Example Networked Video Processing System

Figure 7:
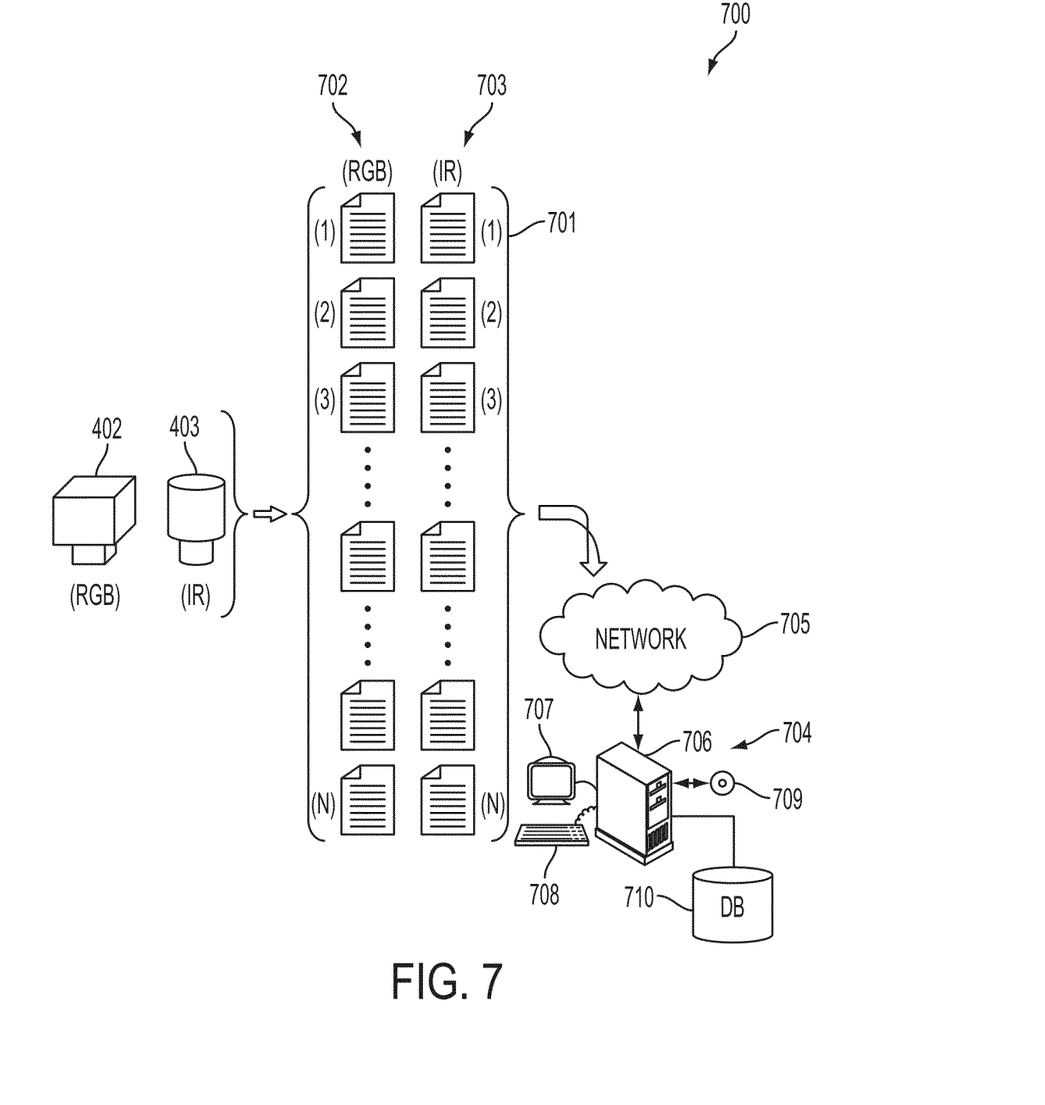
FIG. 7 illustrates an example embodiment of a video processing system wherein the RGB and IR cameras of the video system of FIG. 4 communicate image frames of their respective simultaneously captured videos of a region of exposed skin to a networked computer workstation wherein various aspects of the methods described with respect to the flow diagram of FIG. 5 are performed.

Reference is now being made to FIG. 7 which illustrates an example embodiment of a video processing system 700 wherein RGB camera 402 and IR camera 403 of the video system of FIG. 4 communicate a plurality of RGB image frames 702 and a plurality of IR image frames 702, respectively, (collectively at 701) to a networked workstation 704 wherein various aspects of the methods described with respect to the flow diagram of FIG. 5 are performed.

Workstation 704 receives the video signals comprising IR video and the RGB video (with the image frames of each video ordered from 1 to N where N is the total frames capture for illustration purposes to show the one-to-one correspondence between frames of each of the IR and RGB videos captured simultaneously. If the videos are not captured simultaneously, the videos may be pre-processed to effectuate an alignment there between such that there is a one-to-one correspondence between respective image frames of the IR video signal and the RGB video signal. Workstation 300 may comprise a desktop, laptop, server, mainframe, or the like, as are common in the arts, and is shown having a computer case 706 which houses various components such as, for example, a motherboard (not shown) configured with a central processing unit (CPU), various communication ports, and a memory. Other components not shown which are also internal to computer case 706 are a storage device and a communications link such as a network card to enable various components of workstation 704 to be in communication with one or more remote devices over network 705. The workstation of FIG. 7 is also shown having a display device 707 such as a CRT, LCD, touchscreen device, and the like, along with an alphanumeric keyboard 708 and a mouse (not shown) to effectuate a user input as required. Computer readable medium 709 contains machine readable program instructions for implementing various aspects of the functionality and features of the present method as described herein, and for transporting various aspects of the teachings hereof. Workstation 704 is also in communication with external USB storage device 710 wherein mathematical formulas, variables, numeric values, and the like, as are needed for computation of the various desired cardiac function parameters, are stored along with any computational results. The received videos may also be stored in device 710 for storage and processing.

Computer system 704 is capable of running server software (or housing server hardware) for hosting installed applications, and may further create and/or run a plurality of service proxies for performing various aspects of the teachings hereof. For example, one proxy service would control a timing component of the RGB and IR cameras of FIG. 4 such that the videos acquired thereby are captured simultaneously. Another proxy service would, for example, effectuate communication of the acquired image frames to the workstation for processing via network 705, while yet another proxy service performs any pre-processing on the received videos, as is needed or otherwise desired. The workstation may act as a server to processes that are resident on board one or more controllers providing device-specific control instructions to any of the camera devices.

Figure 8:
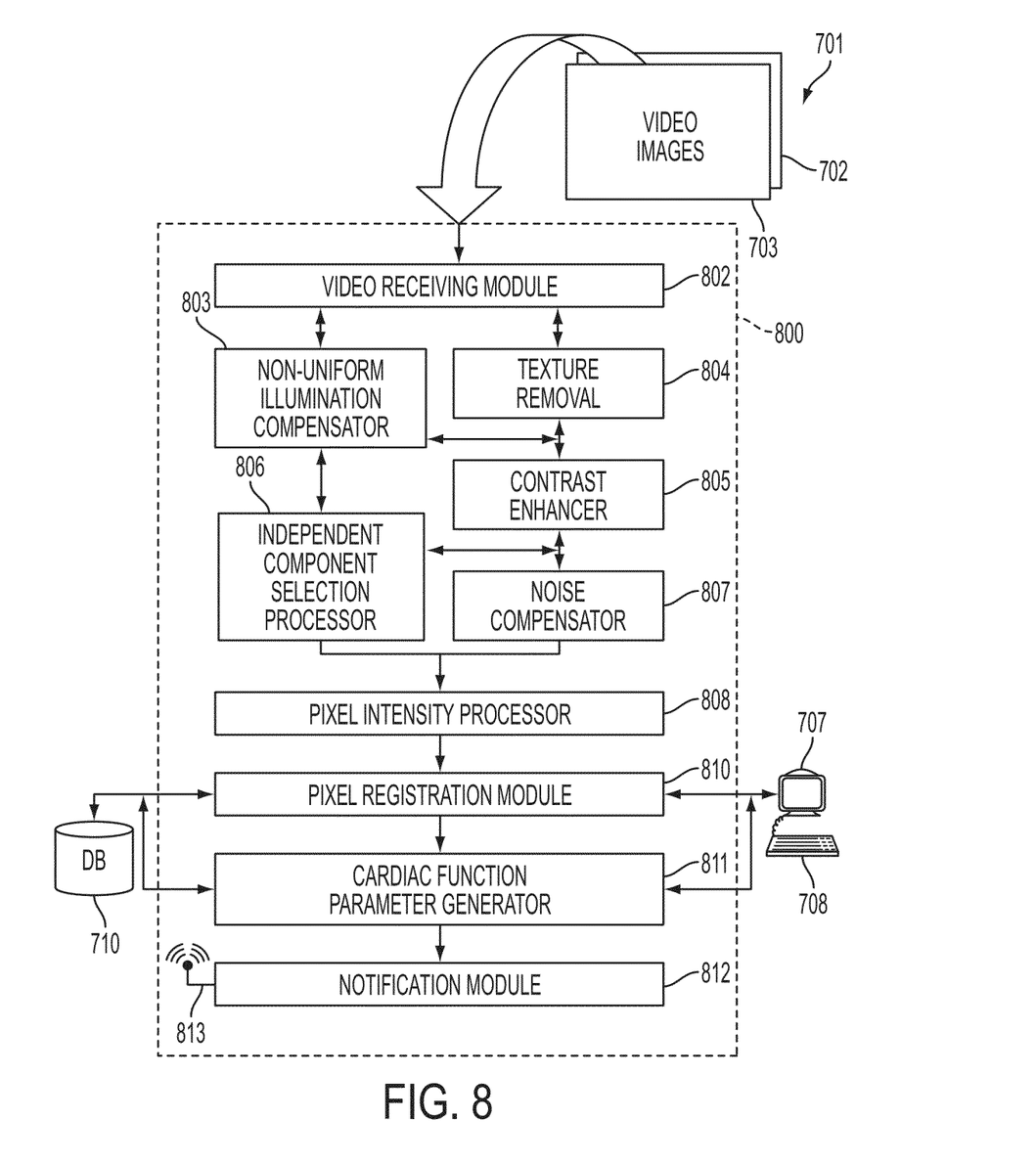
FIG. 8 illustrates a block diagram of one example video analysis system for implementing various aspects of the present method as described with respect to the flow diagram of FIG. 5 and the workstation of FIG. 7.

Special purpose program instructions loaded on workstation 704 cause a central processor thereof to perform any of the determinations, comparisons, calculations, and the like, discussed with respect to the flow diagrams hereof, and/or provide a user or operator with selectable menu options via display 707 or user interface 708, and further provide instructions and/or recommendations which, in turn, are communicated to any of the modules as shown and described with respect to the functional block diagram of the video analysis system of FIG. 8. Information required for such a user selection may be retrieved and/or stored to storage device 710. A user of the workstation of FIG. 7 may use the graphical user interface to identify or otherwise select pixels and/or candidate sub-image sections of one or more video frames for processing or re-processing. Menu options selected by a user and any other selections such as regions of exposed skin, video frames, candidate image subsections, proximal and distal regions, and the like, can be communicated to the workstation. Some or all of the received videos 701 may be played by an operator of workstation 704 and viewed on the display 707, as needed, to facilitate the analysis intended to be performed to obtain the desired cardiac function parameters. Such facilitation may take the form of the operator selecting one or more frames of the video for analysis and processing. The operator may further direct certain video frames or portions of the received video signals to certain modules and/or processors of the video analysis system of FIG. 8. The generated video analysis result(s) may be reviewed by the user. The operator may modify the results as needed and re-direct the modified results back to the same or different modules for further processing or re-processing. It should be appreciated that the workstation has an operating system and other specialized software configured to display a variety of numeric values, text, scroll bars, pull-down menus with user selectable options, and the like, for entering, selecting, or modifying information displayed on display device 707. Upon viewing the computational results, the user may select different regions of interest and provide those to other modules for processing or re-processing. In other embodiments, the generated cardiac function parameter results are provided directly to a server over network 705 and communicated to a user/operator such as, a physician, nurse, technician, cardiac specialist, to name a few. An example embodiment of the various modules and processing units which perform the teachings hereof is shown and discussed with respect to the functional block diagram of FIG. 8.

Block Diagram of Example Video Analysis System

Reference is now being made to FIG. 8 which illustrates a block diagram of one example video analysis system 800, comprising a collection of processing units and modules, for implementing various aspects of the present method as described with respect to the flow diagram of FIG. 5 and the workstation of FIG. 7.

In FIG. 8, the captured RGB and IR videos 701 are communicated to system 800 which provides the video(s) to Video Receiving Module 802 which queues image frames or video signals for processing. Such a buffer may also receive information about, for instance, regions of interest, areas of exposed skin, selected video frames or portions thereof for processing, desired cardiac function parameters to be determined, time/date information, patient cardiac history, user input, threshold values, parameters, mathematical formulas, and the like, as are needed or are otherwise required by any of the modules and processing units of the Video Analysis System 800. Non-Uniform Illumination Compensator 803 retrieves one or more image frames of the video from the buffer of Video Receiving Module 802 and pre-processes the images to compensate for non-uniform illumination due to a curvature of a surface of the region of exposed skin. Compensator Module 803 may also be configured to pre-process one or more image frames in order to compensate for motion induced blur, imaging blur, or slow illuminant variation. Texture Removal Processor 804 executes a smoothing algorithm on some or all of the video images to remove the texture of skin from the surface of the region of exposed skin. Texture Removal Processor 804 may smooth the video retrieved directly from the buffer of Video Receiving Module 802 and provide the pre-processed videos directly to Compensation Module 803 or, alternatively, receive the compensated video from Compensation Module 803. Such embodiments will depend, to a large extent, on the desired cardiac function parameters intended to be obtained by an analysis of the video and the user's preferred system configuration. In this particular embodiment, Contrast Enhancer 805 retrieves the processed video and enhances a contrast thereof. Systems and methods are well established which can effectively increase or decrease a brightness and enhance a contrast of a video or an image frame of a video. Independent Component Selection Processor 806 is utilized for those embodiments wherein it is the user's intention to emphasize certain content in the video such as, for example, a region containing larger blood vessels, and the like. Noise Compensation Processor 807 is provided for those embodiments where the user has determined that camera related noise or environmental factors are adversely affecting the video signals and compensation is desired. The post-compensated video contains environmentally compensated video signals for each processed image frame. Pixel Intensity Processor 808 receives the pixel intensity values measured by the IR channels of the video system and processes the intensity values to generate a vascular binary mask that indicates the location of pixels corresponding to the vascular pathway of the subject within the region of exposed skin for each of the image frames of the processed IR video. A user may select a desired sequence of IR image frames for the computation of the vascular binary mask. Pixel Registration Module 810 receives the IR image and proceeds to register pixels of the IR with pixels of the images captured by the visible channels such that the subject's vascular pattern in the identified region of exposed skin can be isolated in each of the same corresponding frames of RGB video. In one embodiment, registering the IR images with data output by the visible channels involves matching corresponding features in each of the channels used to acquire the video signal. The registered pixels corresponding to the identified vascular pattern in each of the processed image frames is stored to storage device 710 and, in this embodiment, is communicated to display device 707 of the workstation of FIG. 7 for review by the user. Upon viewing these results, the user may select different regions, different sets of image frames, provide input, adjust parameters, and the like, and provide that input back to various modules of system 800 for processing or re-processing. Cardiac Function Parameter Generator 811 retrieves the processed image from storage device 710 and proceeds to process pixels associated with blood vessels of the vascular network such that the one or more desired cardiac function parameters can be determined for the subject. These results are also displayed on display 707. The results may be communicated to the visual display device in real-time or processed offline. In this embodiment, Notification Module 812 receives the determined cardiac function parameters and, if the computed parameters are not within threshold set by, for example, the subject's cardiac specialist, then a notification signal is sent using, for example, Transmission Element 813, which may assume any of a wide variety of communication elements depending on the design of the system wherein the teachings hereof find their intended uses. Notification may further involve initiating an audible sound which provides an indication to the user or specialist that the determined cardiac function parameter(s) require attention. Such a notification may take the form of a canned audio message or, for instance, a bell tone or a sonic alert being activated, or initiating a visible light which provides an indication such as, for instance, a blinking colored light. The communicated notification message can be a text, audio, and/or video message. Such embodiments are intended to be encompassed within the scope of the appended claims.

It should be appreciated that various modules of the block diagram of FIG. 8 designate a system which may comprise software and/or hardware designed to perform one or more specific functions. A plurality of modules may collectively perform a single function. A module may have specialized processors for reading machine executable program instructions for performing their intended function. A module may comprise a single piece of hardware such as an ASIC, electronic circuit, or special purpose computer. The functionality of a plurality of modules may be executed by either a single special purpose computer or a plurality of special purpose computers operating in parallel. Connections between modules include both physical and logical connections. Modules may further include one or more software/hardware modules which may further comprise an operating system, drivers, device controllers, and other apparatuses some or all of which may be connected via a network. Video Analysis System 800 may be connected to a server via a network such as a LAN, a WAN, or the like.

Any of the features or functions of the above-described embodiments may comprise, in whole or in part, a special purpose computer which includes a processor capable of executing machine readable program instructions for carrying out one or more aspects of the teachings hereof. Such a special purpose computer may comprise, for example, a micro-processor, micro-controller, device driver, an electronic circuit, or an ASIC designed to perform some or all of the methods hereof. All or portions of the diagrams of the present system and method, as illustrated herein, may be implemented partially or fully in hardware in conjunction with machine executable instructions in communication with various components of such a system. The exact nature of the implementation will depend on the image processing environment wherein the present method finds its uses. Such a system can be integrated, in whole or in part, with any of a number of computing devices including those in a networked environment. All or portions of the flow diagram of FIG. 5 and the block diagram of FIG. 8 may be implemented partially or fully in hardware in conjunction with machine executable instructions in communication with various components of such a system.

The teachings hereof can be implemented in hardware or software using any known or later developed systems, structures, devices, and/or software by those skilled in the applicable art without undue experimentation from the functional description provided herein with a general knowledge of the relevant arts. The teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system, specialized programs or leverage off-the-shelf computer graphics software such as that in Windows, Java, or from a server or hardware accelerator or other image processing devices.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodologies described herein. The article of manufacture may be included as part of a computer system, an operating system, a plug-in, or may be shipped, sold, leased, or otherwise provided separately either alone or as part of an add-on, update, upgrade, or product suite.

It will be appreciated that various of the above-disclosed and other features and functions, or alternatives thereof, may be combined into other systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for determining a cardiac function parameter from a video of a subject of interest acquired in a non-contact remote sensing environment, the method comprising:
    receiving video of a region of exposed skin of the subject of interest being monitored for cardiac function, said video having been captured using a video system comprising at least one color video camera that outputs data comprising color values collected for color pixels by at least one visible channel, and at least one infrared (IR) video camera that outputs data comprising IR pixel intensity values collected for IR pixels by at least one infrared channel;
    processing said IR pixel intensity values to generate a vascular binary mask that indicates the location of pixels corresponding with a vascular pathway of the said subject within said region of exposed skin;
    registering said IR pixels with color pixels to isolate vascular pattern of the object in said video; and
    processing pixels associated with said isolated vascular pattern to determine at least one cardiac function parameter for said subject, said processing comprising:
        integrating information being carried by said color pixels and IR pixels along vessels of said vascular pattern with respect to time and obtaining a resulting signal;
        normalizing said resulting signal with respect to a value derived from apriori knowledge of cardiac history of said subject;
        converting said normalized signal to a time-series signal; and
        isolating desired components of interest in said time-series signal via independent component selection.

2. The method of claim 1, wherein said color video camera and said infrared video camera are integrated into a single video camera.

3. The method of claim 1, wherein said color video camera and said infrared video camera simultaneously capture said video in both visible and infrared wavelength ranges.

4. The method of claim 1, further comprising identifying said region of exposed skin using any of: object identification, pixel classification, material analysis, texture identification, and pattern recognition.

5. The method of claim 1, wherein, in advance of generating said vascular binary mask, further comprising processing said video to compensate for non-uniform illumination due to a curvature of a surface of said region of exposed skin.

6. The method of claim 1, wherein registering said infrared pixels with color pixels comprises matching corresponding features in each of said infrared pixels and color pixels.

7. The method of claim 1, wherein said cardiac function parameter comprises any of: arterial pulse, pulse frequency, pulse transit time, cardiac output, blood pressure, vessel diameter, blood density, vessel blockage, and peripheral neuropathy.

8. The method of claim 1, further comprising processing said video to remove a texture of skin on a surface of said region of exposed skin via a smoothing technique.

9. The method of claim 1, further comprising pre-processing said video to compensate for any of: a motion induced blur, an imaging blur, and slow illuminant variation.

10. The method of claim 1, wherein said infrared channel includes wavelength ranges of any of: near infrared (NIR), short wave infrared (SWIR), mid-wave infrared (MWIR), and long wave infrared (LWIR).

11. The method of claim 1, further comprising any of: enhancing a contrast of said video, removing undesirable environmental noise from said video, and filtering said video via independent component selection to emphasize desired content in said video.

12. A system for determining a cardiac function parameter from a video of a subject of interest acquired in a non-contact remote sensing environment, the system comprising:
    a video system comprising at least one video camera that outputs data comprising color values collected for color pixels by at least one visible channel, and at least one infrared (IR) video camera that outputs data comprising intensity values collected for IR pixels by at least one infrared channel; and a processor in communication with said video camera system and a memory, said processor executing machine readable instructions for performing:

receiving video of a region of exposed skin of the subject of interest being monitored for cardiac function, said video having been captured using said video system;

processing said IR pixel intensity values to generate a vascular binary mask that indicates the location of pixels corresponding with a vascular pathway of said subject within said region of exposed skin;

registering said vascular binary mask with color pixels to isolate said vascular pattern of said subject in said video; and processing pixels associated with said isolated vascular pattern to determine at least one cardiac function parameter for said subject, said processing comprising:

integrating information being carried by said color pixels and said IR pixels along vessels of said vascular pattern with respect to time and obtaining a resulting signal;

normalizing said resulting signal with respect to a value derived from apriori knowledge of cardiac history of said subject;

converting said normalized signal to a time-series signal; and isolating desired components of interest in said time-series signal via independent component selection.

13. The system of claim 12, wherein said color video camera and said infrared video camera are integrated into a single video camera.

14. The system of claim 12, wherein said color video camera and said infrared video camera simultaneously capture said video in both visible and infrared wavelength ranges.

15. The system of claim 11, further comprising identifying said region of exposed skin using any of: object identification, pixel classification, material analysis, texture identification, and pattern recognition.

16. The system of claim 11, wherein, in advance of generating said vascular binary mask, further comprising processing said video to compensate for non-uniform illumination due to a curvature of a surface of said region of exposed skin.

17. The system of claim 12, wherein registering said infrared pixels with color pixels comprises matching corresponding features in each of said infrared pixels and color pixels.

18. The system of claim 11, further comprising processing said video to remove a texture of skin on a surface of said region of exposed skin via a smoothing technique.

19. The system of claim 11, wherein said cardiac function parameter comprises any of: arterial pulse, pulse frequency, pulse transit time, cardiac output, blood pressure, vessel diameter, blood density, vessel blockage, and peripheral neuropathy.

20. The system of claim 11, further comprising pre-processing said video to compensate for any of: a motion induced blur, an imaging blur, and slow illuminant variation.

21. The system of claim 12, wherein said infrared channel includes wavelength ranges of any of: near infrared (NIR), short wave infrared (SWIR), mid-wave infrared (MWIR), and long wave infrared (LWIR).

22. The system of claim 11, further comprising any of: enhancing a contrast of said video, removing undesirable environmental noise from said video, and filtering said video via independent component selection to emphasize desired content in said video.

* * * * *